United States Patent [19]

Massana

[11] 4,290,151
[45] Sep. 22, 1981

[54] ADJUSTABLE ANNULAR PROSTHESIS FOR CARDIAC SURGERY

[76] Inventor: Miguel P. Massana, c/o Pfizer Inc., 235 E. 42nd St., New York, N.Y. 10017

[21] Appl. No.: 171,059

[22] Filed: Jul. 22, 1980

[30] Foreign Application Priority Data

Jul. 31, 1979 [ES] Spain ............................... 244.903[U]

[51] Int. Cl.$^3$ .............................................. A61F 1/22
[52] U.S. Cl. ......................................................... 3/1.5
[58] Field of Search ...................... 3/1.5, 1; 128/334 R

[56] References Cited

U.S. PATENT DOCUMENTS

| | | | |
|---|---|---|---|
| 3,656,185 | 4/1972 | Carpentier | 3/1.5 |
| 4,042,979 | 8/1977 | Angell | 3/1.5 |
| 4,055,861 | 11/1977 | Carpentier et al. | 3/1.5 |
| 4,164,046 | 8/1979 | Cooley | 3/1.5 |
| 4,217,665 | 8/1980 | Bex et al. | 3/1.5 |

OTHER PUBLICATIONS

Burr et al., "The Mitral Plication Suture," The Journal of Thoracic and Cardiovascular Surgery, vol. 73, No. 4, pp. 589–595 (Apr. 1977).

Duran et al., "Clinical and Hemodynamic Performance of a Totally Flexible Prosthetic Ring for Atrioventricular Valve Reconstruction," *Annals of Thoracic Surgery*, vol. 22, pp. 458–463 (1976).

Shore et al., "Results of Mitral Valvuloplasty with a Suture Plication Technique," *The Journal of Thoracic and Cardiovascular Surgery*, vol. 79, No. 3, pp. 349–357 (Mar. 1980), read at the Annual Meeting of the American Association for Thoracic Surgery, Boston, Mass., Apr. 30 to May 2, 1979.

*Primary Examiner*—Ronald L. Frinks
*Attorney, Agent, or Firm*—Francis X Murphy; Charles J. Knuth; Lawrence C. Akers

[57] ABSTRACT

An adjustable annular prosthesis for use in the surgical correction of atrioventricular orifice defects is disclosed and claimed.

1 Claim, 4 Drawing Figures

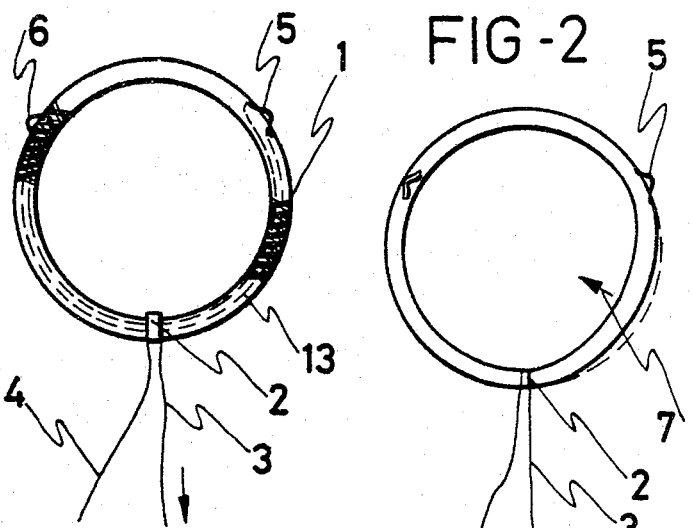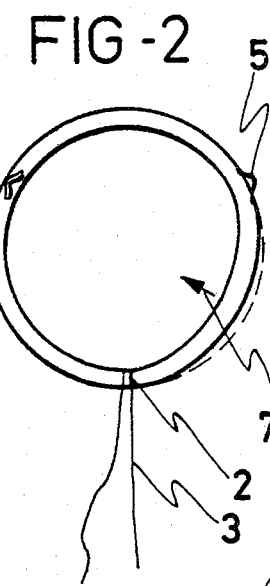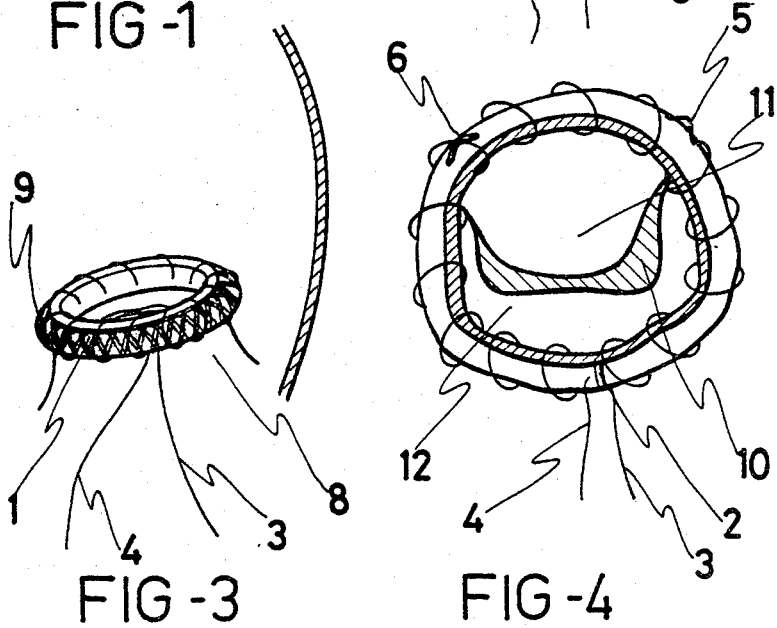

ADJUSTABLE ANNULAR PROSTHESIS FOR CARDIAC SURGERY

BACKGROUND OF THE INVENTION

This invention is related to an adjustable annular prosthesis for use in the surgical correction of defects in the atrioventricular orifices, i.e. the mitral valve and the tricuspid valve. One of the most frequent causes of such defects is rheumatic fever, which can produce the retraction and consequent alteration of the atrioventricular orifices. They may also be caused by a bacterial inflammation of the heart known as endocarditis, be effected in the final phase of syphilis or arterial sclerosis, or be congenital.

Artrioventricular orifice defects are of two general types, which may be present separately or together. A narrowing of stenosis, for example of the mitral valve connecting the left auricle and the left ventricle, causes accumulation of blood in the left auricle, as a result of which the heart cannot operate efficiently. On the other hand, if the mitral valve does not close, some of the blood in the left ventricle flows back into the left auricle when the ventricle contracts, thus generating a condition known as valvular insufficiency. Mitral insufficiency is the defective closing of the mitral valve. Once established, it is a progressive disease.

The heart attempts to compensate for these atrioventricular orifice defects by hypertrophy, followed by dilation with enlargement of the cavities. The common symptoms are shallow respiration and palpitations under stress.

The distension of the auricular cavity and the valvular insertion region caused by valvular insufficiency increases the inefficiency of the valves, thus increasing regurgitation. A vicious cycle is established which must be interrupted in order to avoid the progressive deterioration of the patient.

Numerous techniques of plastic surgery have been developed for the conservative treatment of atrioventricular orifice defects. The best long-term results have been provided by annuloplasty with support by unstretchable rings, some non-deformable and others flexible.

Most of the annular prostheses used up to now are of an unchangeable caliber, in which effective correction depends to a great extent on the skill employed in the distribution of the suture. The functional result can only be verified at the end of the operation, that is to say when the result can no longer be changed without recourse to replacement of the prosthesis.

As a result, errors by way of excess are frequently committed by selecting excessively large diameters because of the suspicion of a stenosis, or excessively small diameters in search of greater security.

Taking into account the fact that a corrective operation on either the mitral valve or the tricuspid valve between the right auricle and right ventricle, the structures of which valves are similar, requires complex and fatiguing work on the part of the surgical team resulting in a risk to the patient which increases with the duration of the operation, there is fully understood the serious drawback represented by replacement of the prosthesis when a mistake due to too large or too small a size is noted after completion of the operation.

There is no doubt that the solution to the problem in question resides in being right at the start, that is in implanting an annuloplasty which provides a perfect fit so that subsequent correction is not necessary. However, since this is not a matter which can be measured a priori without skillful execution, such a fit, aside from pure accident, will only be obtained if the prosthesis is adjustable. However, a mitral or tricuspid insufficiency does not occur uniformly or, stated differently, the defective closing is zonal and irregular. Therefore it does not suffice to provide a ring whose diameter is reducible, but it is necessary that the ring be adjustable in such a manner that its radius is modified in those arcuate zones or sectors in which the defect is present.

U.S. Pat. No. 4,042,979 discloses an adjustable annular valvuloplasty ring that can be used to alleviate certain of the above-mentioned difficulties. The structure of this prior art article is, however, substantially different from that of the annular prosthesis of the present invention.

SUMMARY OF THE INVENTION

It is an object of the present invention to provide an inextendible and flexible annular prosthesis or annuloplasty which can be adjusted at the time of the operation, thus reestablishing a perfect fit in the valve in question.

This and other objects of the invention are realized with a novel adjustable annular prosthesis for cardiac surgery comprising a tubular body of a textile nature which is biocompatible with the human body, which tubular body is woven in longitudinally and diametrically expandable manner so that its diameter decreases when the tubular body is stretched and increases when it is contracted. Said tubular body has its ends sewn together forming a ring which is provided in its interior with a flexible filiform string, which string is nonstretchable and extends to the exterior of the tubular body, preferably on both sides of the seam leaving two loose ends. Approximately 130° from its respective loose or protruding ends, the flexible string is undulated, extending to the exterior of the tubular body and then penetrating again into the interior, thus constituting retention points of the string which differentiate zones of contraction during use of the ring when the latter is sutured in the atrioventricular valves.

DETAILED DESCRIPTION OF THE INVENTION

In order to facilitate an understanding of what has been set forth above, the invention will be described in detail with reference to a preferred embodiment thereof. Reference to this embodiment does not limit the scope of the invention, which is limited only by the scope of the claims. In the accompanying set of drawings:

FIG. 1 is a plan view of a prosthesis constructed in accordance with the invention;

FIG. 2 is a plan view of a prosthesis ring which has been dimensionally altered to effect a correction;

FIG. 3 is a perspective view of an implantation of the ring around a mitral valve; and.

FIG. 4 is a plan view of the implantation of the prosthesis, adapted to the contour of a mitral valve.

Referring to FIG. 1, the adjustable annular prosthesis for cardiac surgery comprises a tubular body of textile nature 1 which has its ends fastened together at seam 2 to form a ring. In the interior of tubular body 1 is provided a filiform string 13 which has loose ends 3 and 4 and is undulated to form retention points 5 and 6.

As shown in FIG. 2, when the end 3 is pulled the space contained between retention point 5 and seam 2 is deformed, contracting and narrowing as shown by arrow 7.

In accordance with FIG. 3, ring 1 is implanted around the body of mitral valve 8 and secured to it by means of suture 9. Once the annuloplasty has been so secured, it suffices to correct the valve defect with one or the other end 3 or 4 or with both, finally tying them in order to reestablish the valve fit.

In FIG. 4, the zone 10 marked by oblique hatching shows the defective closure or fit between the edges of the cusps 11 and 12 of the valve, clearly indicating that the correction must be established by means of both ends 3 and 4, correcting the arc included between the points 2-5 and 2-6 until the fit is reestablished.

I claim:

1. An adjustable annular prosthesis for cardiac surgery comprising
   a tubular body of textile material biocompatible with the human body, said tubular body being woven in such a manner that it is longitudinally and diametrically expandable, and the ends of said tubular body being sewn together at a seam to form a ring, and
   a filiform string provided in the interior of said tubular body and extending to the exterior thereof at two exit points on opposite sides of said seam so as to leave two loose ends, said string being undulated twice at approximately 130° from its respective exit points, extending to the exterior of the tubular body and then penetrating again into the interior thereof, thereby providing retention points of the string which differentiate zones of contraction during use of the prosthesis when the latter is sutured to an atrioventricular valve.

* * * * *